United States Patent [19]

Miller

[11] Patent Number: 5,681,343

[45] Date of Patent: Oct. 28, 1997

[54] BALLOON CATHETER AND INFLATION METHOD

[75] Inventor: Jay F. Miller, Miramar, Fla.

[73] Assignee: Cordis Corporation, Miami Lakes, Fla.

[21] Appl. No.: 556,206

[22] Filed: Nov. 9, 1995

Related U.S. Application Data

[62] Division of Ser. No. 294,659, Aug. 23, 1994, Pat. No. 5,490,838, which is a continuation of Ser. No. 78,511, Jun. 16, 1993, abandoned.

[51] Int. Cl.⁶ .................................................. A61M 29/00
[52] U.S. Cl. ............................................. 606/192; 604/96
[58] Field of Search ............................... 604/96, 97, 98, 604/100, 111, 103, 280, 281, 282; 606/194, 195, 197, 191, 192

[56] References Cited

U.S. PATENT DOCUMENTS

| | | |
|---|---|---|
| 3,426,744 | 2/1969 | Ball . |
| 3,833,003 | 9/1974 | Taricco . |
| 4,143,651 | 3/1979 | Patel . |
| 4,624,657 | 11/1986 | Gould et al. . |
| 4,637,396 | 1/1987 | Cook . |
| 4,697,573 | 10/1987 | Schiff . |
| 4,917,088 | 4/1990 | Crittenden . |
| 4,994,072 | 2/1991 | Bhate et al. . |
| 5,108,415 | 4/1992 | Pinchuk et al. . |
| 5,112,304 | 5/1992 | Barlow et al. ........................... 604/96 |
| 5,171,299 | 12/1992 | Heitzmann et al. . |
| 5,549,551 | 8/1996 | Peacock, III et al. ................. 604/96 |

*Primary Examiner*—Michael Buiz
*Assistant Examiner*—Kevin Truong
*Attorney, Agent, or Firm*—Gerstman, Ellis & McMillin, Ltd.

[57] ABSTRACT

A balloon catheter defines a balloon having a cylindrical outer surface of a diameter essentially no greater than the diameter of the tubular shaft. Additionally, a method is disclosed in which one inserts a catheter into the arterial system of a patient, and increasingly pressurizes a balloon made of work-hardenable material to elastically expand the balloon to such a first pressure that sufficient work-hardening takes place in the expanding balloon to cause the diameter of the balloon to substantially cease its expansion in response to a pressure range increasing from the first pressure. One then terminates the increase of the pressure at that point to cause the catheter to assume a first, predetermined maximum diameter. Catheter balloons can each be expanded to two different, known, work-hardened diameters by this invention.

9 Claims, 1 Drawing Sheet

BALLOON CATHETER AND INFLATION METHOD

CROSS REFERENCE TO RELATED APPLICATION

This is a division of application Ser. No. 08/294,659, filed Aug. 23, 1994, Pat. No. 5,490,838, which in turn is a continuation of application Ser. No. 08/078,511 filed Jun. 16, 1993, which is now abandoned.

BACKGROUND OF THE INVENTION

Balloon catheters find widespread use in the medical field. This invention pertains to balloon catheters which are particularly used in angioplasty or PTCA, where the catheter is inserted into a blood vessel of the patient, positioned, and the balloon is expanded to widen the artery, typically in a stenotic area.

To accomplish this, it is particularly important in the field of angioplasty for the catheter to be initially as small as possible in the area of the catheter balloon, to permit insertion of the catheter through narrow apertures in the artery, such apertures being often surrounded by the stenosis. Catheters with conventional balloons have been sometime incapable of penetrating a small aperture through a stenosis, because, even though the balloon is folded and collapsed, it is slightly larger than the remainder of the catheter shaft, and thus cannot pass through the stenosis.

Also, the surgeon often must estimate the desired size of balloon inflation needed for a particular clinical situation. For this reason various angioplasty catheters with differently sized balloons are available. Often, the surgeon has to remove one catheter with one inflated size of a balloon and replace it with a catheter having a balloon of different inflated size. Typically, balloons of the prior art inflate to a given desired, predetermined size because commercial angioplasty balloons are generally made of flexible but non-resilient plastic materials. There is a significant need for balloons to have a predetermined, maximum size to avoid overinflation.

Thus, in many clinical situations a first catheter balloon that is inserted may turn out to be too small, or it may be desired for the first step of inflation to be only to a certain, smaller amount than a later inflation step. In either circumstance, another catheter balloon of larger size must be brought to bear, which either requires complex, double balloon catheters having a larger shaft, or a new catheter altogether.

In accordance with this invention, a catheter is provided which can be of very small shaft diameter, for example no more than 0.03 inch and preferably less, while at the same time carrying a catheter balloon which is initially substantially no larger than the diameter of the catheter shaft. Furthermore, by this invention, it becomes possible to inflate the same catheter balloon to two different predetermined, maximum diameters. The surgeon can reliably know the maximum diameter of the inflated balloon in predetermined circumstances from the inflation pressure applied, to avoid the danger of the balloon assuming an excessively large diameter for a particular clinical situation. Nevertheless, the same balloon may be inflated to more than one predetermined maximum diameter, so that the catheter of this invention has a greatly increased flexibility of use in surgical procedures.

DESCRIPTION OF THE INVENTION

By this invention, a method is provided which comprises the steps of inserting a catheter into the arterial system of a patient, and increasingly pressurizing a lumen of the catheter up to a first pressure, to cause a work-hardenable portion of the catheter to elastically expand. This first pressure expands the catheter to such a degree that sufficient work-hardening takes place in the expanding catheter portion, to cause the diameter of the catheter portion to substantially cease its expansion in response to a range of pressures increasing from the first pressure. In other words, for a range of elevated internal catheter balloon pressures, including the first pressure, the balloon ceases to significantly expand as the pressure rises, because of work hardening of the balloon wall. When this desired first pressure is reached, or slightly above it, one terminates the increase of balloon pressure at that point.

As the result of this, the catheter portion assumes a first, predetermined maximum diameter which is a function of the first pressure, or a pressure slightly above the first pressure. For this reason, the surgeon can reliably know that if he applies the given, predetermined pressure to the lumen to inflate the work-hardenable balloon portion of the catheter, the catheter portion will inflate to no more than the first predetermined, maximum diameter. The diameter of the catheter portion at this pressure may of course be less it is held to less of a diameter by a resistant stenosis or the like.

Thus, the surgeon can operate safely with this catheter, even though the expandable, work-hardenable portion is a material that expands elastically, contrary to the successful commercial balloons of the prior art which are flexible but non-elastic, so that they expand to a predetermined diameter simply by full inflation rather than by elastic expansion.

As a desirable, added feature of this invention, one can thereafter resume the step of increasingly pressurizing the catheter lumen up to a second pressure which is higher than the first pressure. The effect of this is to cause the catheter portion to resume its elastic expansion from the first maximum diameter, up to a point where the diameter of the catheter portion then again substantially ceases to expand with a pressure increasing from the second pressure.

Many elastically expandable, typically crystalline materials exhibit this characteristic of work hardening, and then expanding again, and then once again becoming resistant to expansion with increasing pressure at a point that is not far from their breaking point. However, by this invention, one stays below the breaking point pressure, again terminating the increase of the pressure at about the second pressure, where the second flattening phenomenon takes place. Thus, the catheter portion assumes a second predetermined diameter at this second pressure, so that the surgeon can reliably know that by applying that second, predetermined pressure, the catheter is assuming a second maximum diameter no greater than another predetermined value.

Thus, the surgeon is capable of using the same balloon to inflate to two different known, maximum diameters by control of pressure. It can thus be used in a wider range of clinical procedures, and may often eliminate the need for catheter replacement during angioplasty procedures.

Also by this invention, a balloon catheter is provided which defines a tubular shaft having an inflation lumen and a balloon communicating with the inflation balloon. The balloon comprises a tube having a smooth, cylindrical outer surface of a diameter which is essentially no greater than the diameter of the tubular shaft.

Preferably, the balloon is capable of elastic expansion, to typically at least double its diameter upon pressurization of the lumen at typically about 5 to 10 psi. The catheter balloon is made of a plastic formulation which is capable of work-hardening upon such elastic expansion.

Plastic materials which are capable of such work-hardening are well-known, being typically those materials which have a relatively high crystallinity, so that they are orientable by stretching to change their physical characteristics. This phenomenon is commercially used in other forms of plastic processing, for example biaxial orientation of containers, which causes cloudy plastics to become crystal clear, stiffer, and stronger. Typical plastics which may be used in accordance with this invention include nylon or polyethylene materials, as well as numerous others known to the art.

Thus, by this invention, it is possible to provide a catheter which has a diameter of no more than 0.03 inch, preferably a diameter of no more than 0.021 inch or less, which catheter is capable of penetrating deeply into the smaller arteries of the heart, or elsewhere if desired such as the brain. Because the catheter balloon of this invention expands in an elastic manner, it does not comprise a folded membrane which is tightly collapsed as in the prior art, but can comprise a structure having initially a smooth, cylindrical outer surface with a diameter essentially no greater than the diameter of the tubular catheter shaft. Then, upon inflation, elastic expansion takes place. Preferably, work-hardening characteristics of the catheter balloon material permit the use of the methods described above with the catheter of this invention, to achieve the desirable results discussed herein.

DESCRIPTION OF SPECIFIC EMBODIMENTS

Figure 1:
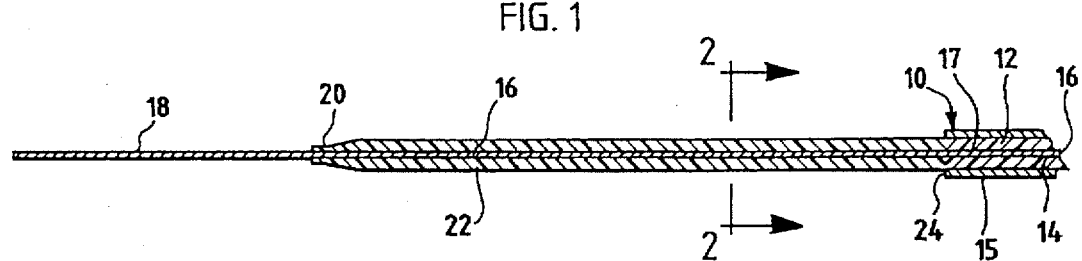
FIG. 1 is a longitudinal sectional view of the distal tip of an angioplasty catheter made in accordance with this invention, in its original configuration.
Figure 2:
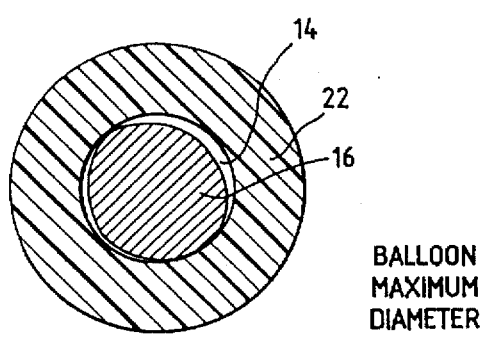
FIG. 2 is a transverse sectional view of the catheter of FIG. 1, taken along line 2—2 of FIG. 1.

Referring to FIGS. 1 and 2, a PTCA catheter 10 is shown, which catheter may be of conventional design except as otherwise indicated herein.

The majority of the length of catheter 10 comprises catheter shaft 12, which is a tube of conventional plastic material defining a lumen 14 through which a guidewire 16 may be loosely emplaced, but slightly undersized relative to lumen 14 so that fluid may pass through lumen 14 despite the presence of guidewire 16.

Figure 3:
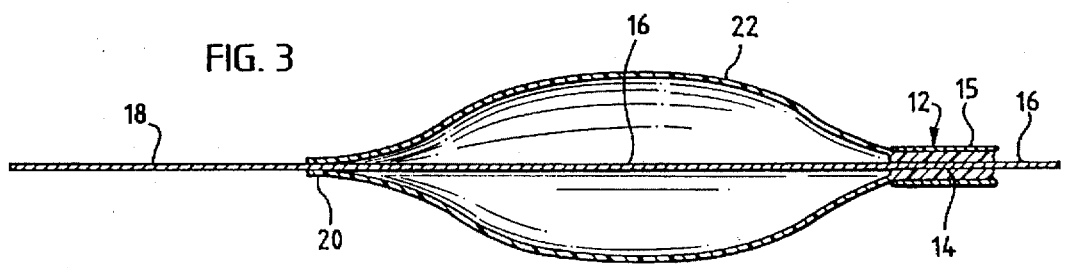
FIG. 3 is a longitudinal sectional view of the catheter of FIG. 1, showing it in inflated condition.

The specific embodiment of the catheter shown is of the balloon-on-wire type, in which guidewire 16 comprises a distal tip wire portion 18, being sealed at distal end portion 20 of the catheter, to seal off lumen 14 at that point. Lumen 14 communicates with a special tubular plastic section 22 of the catheter, sealed at its proximal end 24 to the tubular nonexpansible shaft 12, at its distal end 20 to the guidewire, and serving as the catheter balloon. Tubular shaft 12 is surrounded by a nonexpansible plastic sleeve 15, which terminates at tubular section 22, thus permitting tubular section 22 to expand upon pressurization as shown in FIG. 3. The material of tubular section 22 may be part of an extruded tube which is integral within an inner tubular portion 17 of tubular shaft 12. However, this invention may also be used with other known catheter designs.

In accordance with this invention, the plastic material of tubular section 22 may be made of a substantially crystalline material as described above, which is capable of elastic expansion at the pressures of use, for example 10 or 12 atm. such pressure being applied to the interior of tubular section or balloon 22 through lumen 14. The specific material of section 22 may be a substantially crystalline nylon 8 or polyethylene (P.E.T.), which is capable of such elastic expansion.

Balloon section 22 in its initial configuration is simply in tubular form of similar shape and size to tubular catheter shaft 12, being shown to be of slightly less diameter, although it may also be of equal diameter to catheter shaft 12, or slightly larger to insubstantial degree. Balloon section 22 in its initial configuration can also be seen to have a smooth, cylindrical outer surface rather than being a folded membrane as is used for balloons in current commercial embodiments. Also, catheter balloon 22 typically has a substantially greater wall thickness in its initial configuration than corresponding, non-elastic catheter balloons of the prior art, for example 0.0005 to 0.002 inch.

Accordingly, as shown in FIG. 3, lumen 14 can be pressurized by the surgeon after catheter 10 has been positioned in the arterial system of a patient, with balloon 22 advanced through a stenosis or the like. Because of the small diameter of balloon section 22 in its initial configuration, it can be advanced through the arterial system of the patient as easily or better than the tubular shaft 12 itself, having a smooth, cylindrical outer surface and being of such a low diameter. Thus the catheter section 22 can be advanced into extremely small arteries and through tight stenosis in a manner that is superior to corresponding commercial PTCA catheters that are currently available.

Figure 4:
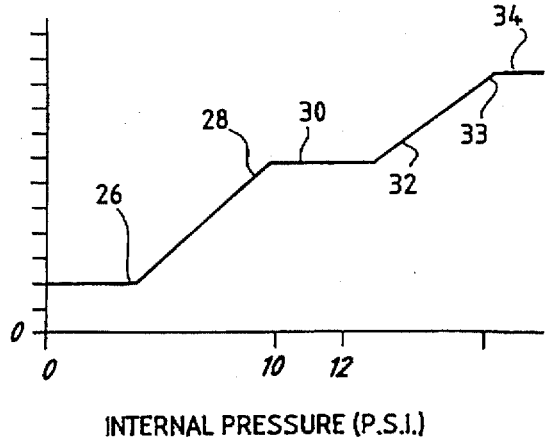
FIG. 4 is a graph showing the increasing diameter of the balloon of the previous drawings as it is subjected to increasing internal pressure.

Upon the inflation shown in FIG. 3, balloon 22 undergoes elastic expansion, stretching and reducing its wall thickness. By this stretching, work-hardening takes place, so that the expanding balloon diameter as a function of internal fluid pressure applied through lumen 14 is as illustrated in FIG. 4. There, it can be seen that the maximum diameter of balloon 22 does not increase with an initial pressure increase, until sufficient pressure 26 begins to cause elastic deformation and expansion of balloon 22. This expansion continues as the internal pressure within lumen 14 and balloon 22 increases until, at a first pressure 28, the amount of work-hardening orientation becomes large enough to strengthen the balloon so that it does not expand with a range of increasing pressure, as illustrated by flattened portion 30 of the curve of FIG. 4. Preferably, this flattened portion of curve 30 will be found at a pressure range on the order of 10 to 12 atm., more or less, which is a good pressure range for the purposes of PTCA, since pressures of this order are good pressures for cracking and expanding coronary artery stenoses. This can be controlled by the specific balloon material selected and its dimensions.

Upon a further increase in pressure, the curve ceases to be flat and moves upward again, as at curve portion 32. Then, with further increasing pressure, for example at a second pressure 33 of >12 atm., the curve will flatten again as at section 34. Upon further pressure increases, the balloon will not expand much further, but rather will typically burst.

Accordingly, it can be seen that catheter balloons made of substantially crystalline materials having a pressure curve of the general shape of FIG. 4 may be reliably designed to exhibit two different, predictable maximum diameters. Accordingly, if the surgeon wishes the balloon to achieve the maximum diameter of curve section 30, he has only to apply to lumen 14 a pressure of 10 to 12 atm, or whatever pressure the particularly designed balloon will require. The surgeon can rely upon the fact that balloon 22 will expand no more than the expected amount in that circumstance.

However, in the event that this amount of balloon expansion turns out to be undesirable or unsuccessful in accomplishing the purpose, the surgeon has the further option of expanding the same balloon to a second, predetermined maximum diameter, as reflected by horizontal curve portion 34, which is achieved at the second pressure 33.

Thus, the surgeon is capable of expanding balloon 22 to the second, larger predetermined maximum diameter simply by raising the pressure in lumen 14 and balloon 22 to the second predetermined pressure 33.

Accordingly it becomes possible for the surgeon to accomplish his purpose with one rather than two PTCA catheters, avoiding the time, the expense, and the possible trauma to the patient involved in removing a first catheter and replacing a second one. Similarly, with catheters having multiple, spaced, balloons, the unnecessary catheter movement from one balloon location to another is avoided. Also, such multiple balloon catheters would have to have multiple lumens to independently control each balloon, which would force the catheters to be of larger diameter, and less accessible to narrow arteries.

The above has been offered for illustrative purposes only, and is not intended to limit the scope of the invention, which is as defined in the claims below.

That which is claimed is:

1. A balloon catheter defining a tubular shaft having a diameter, an inflation lumen, an outer wall with a wall thickness, and a balloon communicating with said inflation lumen, said balloon comprising a tube integral with said shaft and having a cylindrical outer surface of a diameter essentially no greater than the diameter of said tubular shaft, said balloon having a tubular wall thickness that is substantially the same as the wall thickness of said outer wall of the tubular shaft, said balloon being made of a plastic formulation capable of work-hardening upon elastic expansion; and an outer, tubular, non-expansible sleeve which surrounds said tubular shaft but is spaced from said balloon to permit inflation of said balloon by pressurization through said inflation lumen, to cause expansion of said balloon in a manner resulting in work-hardening while said tubular shaft is restrained from said expansion.

2. The catheter of claim 1 in which said balloon and shaft are made of a plastic formulation selected from the group consisting of nylon and polyethylene.

3. The catheter of claim 1 in which said balloon is capable of elastic expansion to at least double its diameter upon pressurization of said inflation lumen to about 10 to 12 atm.

4. The catheter of claim 1 in which said balloon and tubular shaft have a diameter of no more than 0.03 inch.

5. The catheter of claim 4 in which said balloon is made of a plastic formulation selected from the group consisting of nylon and polyethylene.

6. The catheter of claim 5 in which said balloon is capable of elastic expansion to at least double its diameter upon pressurization of said lumen to about 10 to 12 atm.

7. The catheter of claim 6 in which said balloon is made from a single, integral, tubular wall made of said plastic formulation.

8. The catheter of claim 1 in which said balloon is made from a single, integral, tubular wall made of said plastic formulation.

9. A balloon catheter defining a tubular shaft having a diameter, an inflation lumen, an outer wall with a wall thickness, and a balloon communicating with said inflation lumen, said balloon comprising a tube integral with said shaft and having a cylindrical outer surface of a diameter essentially no greater than the diameter of said tubular shaft, said balloon having a tubular wall thickness that is substantially the same as the wall thickness of said outer wall of the tubular shaft, said balloon being made of a plastic formulation capable of work-hardening upon elastic expansion; and an outer, tubular, non-expansible sleeve which surrounds said tubular shaft but is spaced from said balloon to permit inflation of said balloon by pressurization through said inflation lumen, to cause expansion of said balloon in a manner resulting in work-hardening while said tubular shaft is restrained from said expansion, said balloon and shaft being made of a plastic formulation selected from the group consisting of nylon and polyethylene, said balloon being capable of elastic expansion to at least double its diameter upon pressurization of said inflation lumen to about 10 to 12 atmospheres.

* * * * *